United States Patent
Rodrigues et al.

(10) Patent No.: US 11,879,885 B2
(45) Date of Patent: Jan. 23, 2024

(54) ELECTROCHEMICAL MEASUREMENT SYSTEM AND METHOD FOR MONITORING A CONCRETE STRUCTURE

(71) Applicants: IRIS INSTRUMENTS, Orléans (FR); BRGM, Orléans (FR)

(72) Inventors: Romain Rodrigues, Orléans (FR); Julien Gance, Orléans (FR); Ioannis Ignatiadis, Paris (FR); Stéphane Gaboreau, La Ferté-Saint-Aubin (FR); Stéphanie Betelu, Orléans (FR)

(73) Assignee: IRIS INSTRUMENTS, Orléans (FR)

( * ) Notice: Subject to any disclaimer, the term of this patent is extended or adjusted under 35 U.S.C. 154(b) by 207 days.

(21) Appl. No.: 17/628,455

(22) PCT Filed: Jul. 24, 2020

(86) PCT No.: PCT/EP2020/071052
§ 371 (c)(1),
(2) Date: Jan. 19, 2022

(87) PCT Pub. No.: WO2021/014021
PCT Pub. Date: Jan. 28, 2021

(65) Prior Publication Data
US 2022/0260548 A1    Aug. 18, 2022

(30) Foreign Application Priority Data

Jul. 25, 2019 (EP) .................................... 19188380

(51) Int. Cl.
*G01N 33/38* (2006.01)
*G01N 17/02* (2006.01)
(Continued)

(52) U.S. Cl.
CPC ......... *G01N 33/383* (2013.01); *G01N 17/006* (2013.01); *G01N 17/02* (2013.01); *G01N 27/045* (2013.01)

(58) Field of Classification Search
CPC .... G01N 17/02; G01N 17/006; G01N 27/045; G01N 33/383
See application file for complete search history.

(56) References Cited

U.S. PATENT DOCUMENTS

| 10,247,691 B1 * | 4/2019 | Sagüés | G01N 33/383 |
| 2012/0043981 A1 * | 2/2012 | Chiang | G01N 33/38 324/700 |

OTHER PUBLICATIONS

International Search Report dated Oct. 8, 2020, in corresponding to International Application No. PCT/EP2020/071052; 4 pages.
(Continued)

*Primary Examiner* — Alesa Allgood
(74) *Attorney, Agent, or Firm* — Maier & Maier, PLLC (57) ABSTRACT

An electrochemical measurement system for monitoring a concrete structure having a reinforcement bar, including: at least six electrodes to contact the concrete structure's surface, including at least two emitting electrodes to inject electrical signals into the structure and at least four receiving electrodes combined in pairs, each pair receiving electrical signals, originating from an explored zone of the structure located beneath an axis connecting the electrode pairs with its depth depending on the distance between the two electrodes in the pair; an acquisition module to (i) control the electrodes and (ii) acquire and store in a memory the electrical signals; a processing module to calculate, for the electrical signals, induced polarization potential response value(s) and one apparent resistivity value; from these values, process output characteristic(s) of each explored (Continued)

zone; an image reconstruction module to generate an image of the distribution of the output characteristic(s) in the explored zones.

18 Claims, 5 Drawing Sheets

(51) Int. Cl.
*G01N 17/00* (2006.01)
*G01N 27/04* (2006.01)

(56) References Cited

OTHER PUBLICATIONS

Stefan Hurlebaus et al., "Substainability of Bridge Foundations Using Electrical Resistivity Imaging and Induced Polarization to Support Transportation Safety"; Apr. 1, 2014; XP055733288; 162 pages.

N. Wiwattanachang et al., "Monitoring crack development in fiber concrete beam by using electrical resistivity Imaging"; Journal of Applied Geophysics; Elsevier; vol. 75; No. 2; Jun. 10, 2011; pp. 294-304; XP028305428.

Pham Huy Giao et al., "A new method to monitor and determine permeability of concrete based on resistivity and time-domain chargeability measurements"; The 13th SEGJ International Symposium 2018; Apr. 29, 2019; pp. 284-287; XP055733283; https://doi.org/10.1190/SEGJ2018-074.1.

\* cited by examiner

ELECTROCHEMICAL MEASUREMENT SYSTEM AND METHOD FOR MONITORING A CONCRETE STRUCTURE

FIELD

The present invention relates to the field of civil engineering and its various fields of application, such as infrastructure, geotechnics, hydraulics, energy, transport and the environment. In particular, the present invention relates to the field of electrochemical methods for measuring characteristics of concrete structures.

BACKGROUND

Concrete is resistant under compression, as the aggregates efficiently carry the compression load. However, it is weak when undergoes tension so that as the cement holding the aggregate in place can crack, allowing the structure to fail. Reinforced concrete solves these problems by adding steel reinforcing bars, steel fibers, glass fiber, or plastic fiber to carry tensile loads. Thereafter, the concrete is reinforced to withstand the tensile loads upon it. Due to their low cost and wide availability, steel reinforcing bar (commonly referred to as rebar) has been the dominant reinforcing material for the past 50 years.

In the alkaline environment of sound concrete, a passive film will form spontaneously on the surface of the steel, ensuring a good protection from corrosion (low corrosion rates). However, the continuous degradation of concrete due to the ingress of aggressive agents will affect the integrity of the passive layer, resulting in the acceleration of the corrosion rate. Generally, corrosion of steel in concrete is induced either by carbonation (due to the ingress of carbon dioxide in concrete) or by chlorides (in marine environment or due to the use of de-icing salts), resulting in the formation of corrosion products (various iron oxides and hydroxides, collectively referred to as rust). The formation of rust plays an important role in the structural performance and the service life of reinforced concrete as they expand and tend to flake, reducing the bonding between the rebar and the concrete and inducing radial pressure on the concrete, generating cracks on the concrete.

Corrosion of steel in concrete is an electrochemical process involving the oxidation of iron (anode) and generally the reduction of oxygen (cathode), while the concrete pore solution acts as the electrolyte to ensure an electrical connection between anode and cathode.

$$Fe \rightarrow Fe^{2+} + 2e^-  \quad \text{(Eq. 1)}$$

$$\tfrac{1}{2}O_2 + H_2O + 2e^- \rightarrow 2OH^- \quad \text{(Eq. 2)}$$

Hence, the rate at which corrosion occurs can be limited either by the kinetics of the reactions, the availability of oxygen or the flow rate of the ions, and thus on the resistivity of concrete.

The corrosion of the steel rebars is the main cause of damage and early failure of reinforced concrete structures. The prevention and detection of deterioration of concrete infrastructures is one of the greatest challenges. Various non-destructive quantitative techniques based on electrochemical methods have been used for measuring the corrosion rate, in order to predict residual lives and accordingly decide what preventive or repair systems are to be applied.

These techniques are based on the determination of the polarization resistance ($R_p$), a physical parameter directly related to the corrosion phenomenon according to the Stern-Geary relation (Eq. 3).

$$i_{corr} = \frac{B}{R_p} \quad \text{(Eq. 3)}$$

where $i_{corr}$ is the corrosion current density (A/m$^2$) and B is the proportionality constant which can be calculated from the anodic and cathodic Tafel slopes (V/dec).

These methods are the linear polarization resistance (LPR), the galvanostatic pulse (GP) or the potentiostatic pulse (PP), or the electrochemical impedance spectroscopy (EIS). These different techniques are widely used in the laboratory to study the corrosion phenomena of metals and alloys.

The galvanostatic pulse technique was introduced for field application in 1988. This method is a rapid non-destructive polarization technique. An anodic current pulse is applied galvanostatically between the rebar and a counter electrode placed on the concrete surface. The applied current is usually in the range of 10-100 µA. The reinforcement is anodically polarized and the transient potential measured between the reinforcement bar and a reference electrode placed on the concrete surface is recorded until stabilization. The typical pulse duration is between 5 and 30 s for actively corroding rebars, up to 100 s for passive rebars, as longer times are required to reach the steady state. Based on the Randles circuit, the polarization at any time t can be expressed as:

$$E_t = I_{app}\left[R_p * \left[1 - \exp\left(\frac{-t}{R_p C_{dl}}\right)\right] + R_\Omega\right] \quad \text{(Eq. 4)}$$

where $E_t$ is the polarization (V) at any time t (s), $I_{app}$ is the applied constant current (A), $C_{dl}$ is the capacitance of the double layer (F) and $R_\Omega$ is the concrete resistance (Ω). The expression is generally linearized to calculate $R_p$ and $C_{dl}$:

$$\ln(E_{max} - E_t) = \ln(I_{app} * R_p) - \frac{t}{R_p C_{dl}} \quad \text{(Eq. 5)}$$

where $E_{max}$ is the potential value at the steady state (V). A curve fit can also be used to calculate the different parameter (Eq. 6):

$$E_t(t) = K_0 - K_1 \exp\left(\frac{-t}{K_2}\right) \quad \text{(Eq. 6)}$$

with:

$$K_0 = I_{app}(R_p + R_\Omega) \quad \text{(Eq. 7)}$$

$$K_1 = I_{app} R_p \quad \text{(Eq. 8)}$$

$$K_2 = R_p C_{dl} \quad \text{(Eq. 9)}$$

Electrochemical impedance spectroscopy consists of applying a small amplitude alternating potential (or current) of variable frequencies on the rebar and measuring the amplitude and phase-shift of the current (or potential) for each of the frequencies to determine the impedance Z. Impedance is the property related to the opposition of a circuit to an electrical current in AC condition. Each circuit element, i.e. resistor, capacitor or inductor, presents an impedance. If the resistance created by a resistor is independent of the frequency ($Z_R$=R), the resistance created by a capacitor or an inductor depends on the frequency ($Z_C=1/(j\omega C)$ and $Z_L=j\omega L$), which creates a phase shift between the voltage and the current. As the sinusoidal current or voltage can be represented as a rotating vector, the impedance can be divided in two components, a real component and an imaginary component, as follows:

$$Z = Z_{re} + jZ_{im} \quad \text{(Eq. 10)}$$

$$|Z(\omega)| = \sqrt{Z_{re}(\omega)^2 + Z_{im}(\omega)^2} \quad \text{(Eq. 11)}$$

$$\varphi(\omega) = \tan^{-1}\left(\frac{Z_{im}(\omega)}{Z_{re}(\omega)}\right) \quad \text{(Eq. 12)}$$

Different data plots exist to represent the results of EIS analysis. The Nyquist plot is obtained by plotting $Z_{re}$ on the x-axis and $-Z_{im}$ on the y-axis. On this plot, the $R_p$ value is determined at low frequencies when the plot intercept the x-axis (on the right of the plot), with taking into account the resistance of the concrete which is determined at high frequencies (on the left of the plot). In practice, only a part of the low frequencies loop is obtained, and the plot must be extrapolated to obtain the $R_p$ value by using an equivalent electrical circuit (EEC). Often, the capacitor is modeled using a constant phase element (CPE) to consider the non-ideal behavior of the passive layer, with an impedance of:

$$Z_{CPE} = \frac{1}{(j\omega)^\alpha Q} \quad \text{(Eq. 13)}$$

These conventional techniques ("3-electrodes" measurement) require, in order to carry out measurements, that the reference electrode is put on the concrete surface while the rebars act as working electrodes. Therefore, in the case of reinforcement in concrete, these techniques require, if the connections are not readily available, the prior localization of the rebars, the partial breakout of concrete so as to make electrical contact with the reinforcing steel and finally the filling of the opening created after performing the measurements.

While these techniques provide good estimates of corrosion rates for actively corroding reinforcements in a laboratory environment (small sample, core sample), there are several limitations to their use for field application. The first limitation is related to the difficulty of estimating the surface that is polarized during the measurement. However, a good estimate of this surface is essential to convert the polarization resistance into effective corrosion rate (loss of thickness per year). To overcome this problem, an auxiliary electrode—known as the guard ring—can be used for the galvanostatic pulse method to confine the polarization to a known length of the bar, in order to estimate the surface under investigation. However, many studies have highlighted that the guard ring fails to confine the current over the full range of corrosion rates, and often compromised the measurement. Also, techniques based on electrochemical impedance spectroscopy are more difficult to use for field application because of the long measurement time required to obtain a good estimate of the corrosion rate. Indeed, the measurements are made up to low frequencies (less than 10 Hz, generally down to 1 mHz), thus requiring several hours of measurement. Finally, the device requires the use of a reference electrode and a counter electrode of a very large specific surface to ensure the achievement of correct measurements.

In this context, it is therefore of great interest the development of an electrochemical measurement system allowing to implement field measurements and which, in the case of reinforcement in concrete, does not require a direct contact with the rebars. Several techniques have been proposed to estimate the polarization resistance without any connection to the rebar, by using a four-electrode arrangement on the surface of the concrete. The most common configuration is the Wenner configuration, in which the four electrodes are aligned with a constant interelectrode spacing. The two external probes are used to inject the current, while the two internal probes are used to measure the resulting potential difference. Measurements can be performed by imposing a direct current or an alternative current at several frequencies. The first method can be referred as external galvanostatic pulse method—which is similar to the time-domain induced polarization (TDIP) used in geophysics—, while the second method can be referred as external EIS method—which is similar to the spectral induced polarization (SIP) used in geophysics. In four-point configuration, only a part of the current injected at the surface of the concrete polarizes the rebar, the other part flowing in the concrete.

It has been shown that many parameters can influence the distribution of the current in the material, especially the concrete resistivity and the cover depth. As the material is heterogeneous by nature, the knowledge of the resistivity profile along the rebar is required to correctly assess the current that polarize the rebar. For this purpose, a multi-electrode device consisting of an assemblage of single devices with four electrodes can be used to perform an electrical resistivity survey. By using this device, the measured resistivity corresponds to an apparent resistivity that takes into account all the elements in the investigated area. After an inversion process, the real resistivity of the concrete is determined from the measured apparent resistivity.

Hence, the development of a system allowing to accurately determine the corrosion rate without any connection to the rebar is of great interest for fields.

SUMMARY

The present invention relates to an electrochemical measurement system for monitoring a concrete structure comprising:
- at least six electrodes configured to be placed in contact with a surface of the concrete structure and arranged in a predefined spatial configuration; comprising:
  - at least two emitting electrodes configured to inject a plurality of electrical signals into the concrete structure;
  - at least four receiving electrodes configured to be combined in pairs; wherein each pair of electrodes receives a plurality of electrical signals, originating from an explored zone of the concrete structure;
- an acquisition module configured (i) to control the emitting electrodes and receiving electrodes, and (ii) to acquire and store in a memory the plurality of electrical signals;
- a processing module configured to calculate for each plurality of electrical signals at least one induced polarization potential response value and one apparent resistivity value, and from these values, process at least one output characteristic of the concrete structure associated to each explored zone from which the plurality of signals originates;

an image reconstruction module configured to generate an image of the distribution of the output characteristics of the concrete structure in the explored zones.

Advantageously, in the present invention, the apparent resistivity is obtained from the plurality of electrical signals. Resistivity is an intrinsic property of a material that quantifies how strongly it resists or conducts electric current and therefore is independent from the disposition of the electrodes used to acquire the signals. Inversely, the polarization resistance ($R_p$), used in the method presented in the background, depends directly from the relative position of the electrodes used to acquire the signals. This has the main disadvantage that signals acquired with different electrodes spatial dispositions are not directly comparable.

The explored zone of the concrete structure depends on the electrode position and on the concrete resistivity. It can be defined as the zone in which the electrical signals are significantly interacting with concrete and/or reinforcement bars to yield the measurement. In other words, changing the resistivity distribution in the explored zone will change the measurement at the surface. Alternatively, changing the resistivity distribution outside the explored zone will not impact the measurement at the surface. In practice, the explored zone is defined by the value of the Jacobian matrix.

Figure 10:
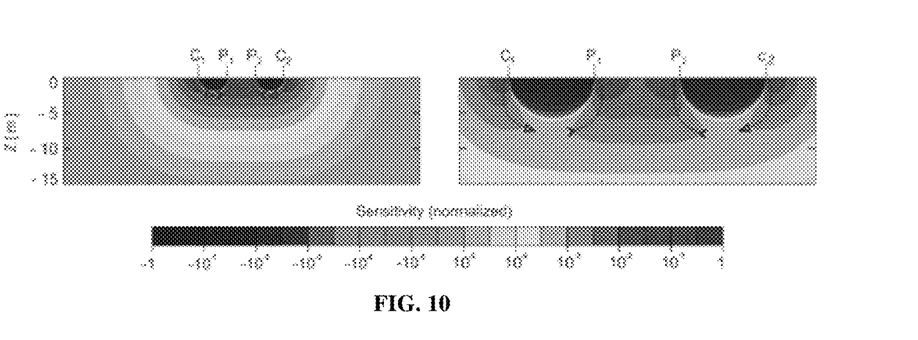
FIG. 10 is an illustration of the explored zone in a specific configuration of electrodes.

FIG. 10 illustrates the shape of explored zone with a configuration for electrodes disposed on the surface and known as Werner α. Two electrodes (C1, C2) are used to inject current and two electrodes (P1 and P2) are used to measure potential. Sensitivity—here: normalized and in a grey scale—is shown as function of depth and position below electrodes. Where sensitivity is low, typically below $10^{-3}$ in absolute value, electric signal is not interacting significantly with sample. The explored zone corresponds to domains where sensitivity is high.

According to one embodiment, the explored zone reached by the inject plurality of electrical signals include whole or part of a reinforcement bar of the concrete structure, and one characteristic of the concrete structure is the corrosion rate of the reinforcement bar. The evaluation of this parameter is particularly advantageous since the corrosion rate has been identified as the most relevant parameter for the corrosion propagation period, during which the rebar corrodes until a maximum tolerable level of damage is reached. Hence, an accurate measurement of the corrosion rate will help to estimate the remaining service life of the structure.

This embodiment requires a previous knowledge of the location of the reinforcement bar inside the concrete structure. Such knowledge may be achieved by previous investigation of the concrete structure surface by means of a system using electromagnetic techniques such as ground-penetrating radar or capacitive technique (cover meter).

According to one embodiment, the processing module is configured to:
calculate apparent resistivity values and apparent chargeability values for each plurality of electrical signals;
receive a model comprising a geometric disposition of the reinforcement bar in the concrete structure, initial values of resistivity and chargeability for the reinforcement bar volumes and initial values of resistivity and chargeability for the concrete volumes;
perform inversion using the model, the apparent resistivity values and the apparent chargeability values so as to obtain the inversed resistivity values and the inversed chargeability values, and from these values, process at least one output characteristic of the concrete structure associated to each explored zone from which the plurality of signals originates; wherein one output characteristic of the concrete structure is the corrosion rate of the reinforcement bar.

The model received by the processing module is also known as starting model wherein the geometric disposition of the reinforcement bar in the concrete structure and the initial values of resistivity and chargeability for the reinforcement bar volumes and initial values of resistivity and chargeability for the concrete volumes represent additional parameters of the inversion model. These additional parameters are used to performed a decoupled inversion.

This additional constraint is advantageous because inversion processes in general are ill-posed problems in mathematics. As a consequence, an infinity of inverted model can explain the apparent measurement. The user must choose one model that is in agreement with his knowledge of the medium. Most of the time, the user chooses smoothest models where the variation of inverted resistivity from one cell to the other are minimized all over the inverted model. In electrical measurements of concrete comprising rebars, the smoothest model is not appropriate as the resistivity may be totally different in the concrete and in the rebar (e.g. going from 1 to 500 Ohm·m). The inversion used is therefore a decoupled inversion where the user authorizes a strong variation of resistivity between two adjacent cells located in the concrete and in the rebar.

The inversion model is a discretized model comprising so-called cells, each cell being associated either to the concrete volume either to the reinforcement bar volume. The initial values of resistivity and chargeability are predefined numerical values associated to each cell of the model.

Initial values of resistivity of the concrete and reinforcement bar strongly depend on the corrosion state of the concrete structure. Notably, the initial values of resistivity of the concrete are different from initial values of resistivity of the reinforcement bars when there is a process of corrosion undergoing in the concrete structure. On the contrary when no corrosion is present the concrete chargeability is close to zero and the only the reinforcement bar chargeability need to be measured.

According to one embodiment, the processing module is configured to use an inversion code using the (inversion) model to obtain the inversed resistivity and the inversed chargeability from which is calculated the polarization resistance $R_p$ then used to obtain the corrosion current $i_{corr}$. This embodiment advantageously allows to obtain the corrosion current value closer to reality. Indeed, the invention code take account for inhomogeneities of the medium (i.e. concrete) and therefore of the fact that current does not follow standard current lines generated in a homogeneous medium. The invention code provides a more accurate estimation of the corrosion current and therefore corrosion rate in a highly heterogenous medium such as concrete. The three or four points measurements only allow to obtain averages values that don't allow to use an inversion code and therefore provides less precise estimation of corrosion current.

The resistivity for the reinforcement bar volumes and resistivity for the concrete volumes may have very different values depending on the structure concrete structure under investigation. For example, the resistivity of the rebar ranges typically between 1 Ohm·m (in corroded conditions) and 10000 Ohm·m (not corroded). The resistivity of the concrete may vary in the same range depending if it is moistened or impregnated with salted water (very conductive) or completely dry (very resistive)

In order to allow a convergence of the calculations of processing module to a realistic model, it is preferable to define the initial values of resistivity and chargeability for the reinforcement bar volumes and the initial values of resistivity and chargeability for the concrete volume according to the resistivity features of the concrete structure under investigation.

In one embodiment, the initial values of resistivity and chargeability for the reinforcement bar volumes and the initial values of resistivity and chargeability for the concrete volumes are determined from apparent measurements of resistivity and chargeability made on the concrete structure.

For example, initial values of resistivity and chargeability for the concrete volume may be estimated placing the electrode on the concrete structure in a confirmation where the receiving electrodes are close to each other so as to avoid receiving the signal produced from the reinforcement bars. The variation of the resistivity as function of the distance between the measuring electrodes may as well be used to evaluate the initial values of resistivity and chargeability for the concrete volume and the reinforcement bar volume.

It is interesting to notice that aim of the present invention is not to correct for the perturbations caused by the presence of rebars in the concrete, as usually done in geophysics, but on the contrary to use the signal from the rebars to obtain information on the corrosion status of the rebars.

According to one embodiment, the processing module is configured to obtain a distribution of the polarization resistance from the apparent resistivity then to obtain the corrosion rate. More precisely, the polarization resistance is used in the Stern-Geary relation in order to obtain the corrosion current density $i_{corr}$ from which is calculated the corrosion rate.

According to one embodiment, the corrosion rate value is obtained from the transient potential obtained during the polarization of the rebar, corrected by the apparent resistivity values. The apparent resistivities will first be inverted in order to obtain a spatial distribution of the true resistivities. Polarization resistance and corrosion rate can then be corrected estimating the distribution of the current with the true resistivities and the polarized area of the rebar. The change in potential during the injection of the direct current can be the result of the change in self-potential values and/or the polarization of the rebar. However, only the polarization of the rebar has to be considered here to determine accurately the polarization resistance.

In the context of the present invention the term image as to be understood broadly as a spatial distribution of values, i.e. at least two values each associated to one spatial position.

According to one embodiment, the injection current I provided through the emitting electrodes is a direct current.

According to one embodiment, the injection current I provided through the emitting electrodes is an alternating current. The use of direct current allows faster measurements which however are less accurate than the ones obtained with alternating current, especially in the case of passive rebars.

According to one embodiment, the direct current I applied through the emitting electrodes ranges from a few µA up to a few mA. The highest current values of a few mA are particularly advantageous in order to obtain an exploitable signal in the case of very corroded rebar where the polarization is very low, in order to increase the signal to noise ratio. However, the resulting potential difference must not exceed 20 mV in order to maintain the linear relationship between the applied current and the corresponding potential.

Hence, the applied current has to be carefully selected. A preliminary measurement may be performed to assess the actual state of the rebar.

According to one embodiment, the alternating current applied through the emitting electrodes ranges from 10 Hz down to 1 mHz. The lower frequency values are necessary to obtain accurate measurements of the polarization resistance, thus on the corrosion rate.

According to one embodiment, the electrodes in one predefined spatial configuration are disposed inline or at least the receiving electrodes are disposed inline.

When the receiving electrodes are disposed inline, the plurality of electrical signals acquired originate from a concrete volume located beneath the axis connecting the electrodes. For this predefined spatial configuration of the electrodes the image generated by the image reconstruction module is a unidimensional (1D) or bidimensional (2D) image representing the distribution of the estimated characteristic of the concrete structure for an in-depth section of the concrete structure below the aligned electrodes.

The measurements of the electrical signals received by the receiving electrodes are used to obtain the resistivity distribution in the concrete structure by calculation processed in the processing module. The representation of resistivity distribution by imaging allows to differentiate areas with different resistivities.

According to one embodiment, the processing of the resistivity distribution provides as output at least one characteristic of the concrete structure in one explored zone such as the carbonation of the concrete, the water content, the presence of cracks, the presence of $Cl^-$ and the like.

According to one embodiment, the characteristic of the concrete structure is at least one of:
cracking, crazing, blistering, delamination, chalking,
air void,
corrosion of the reinforcement bar,
water content or
a transport characteristic selected from the group comprising permeability, diffusivity or porosity.

According to one embodiment, the processing module is further configured to perform pre-processing steps on the acquired signals such as filtering and self-potential correction.

A selective filter, having for example bandwidth between 0 and 10 Hz, allows to remove power line signals that can be measured in rebars and which perturbates the measurements.

According to one embodiment, the electrodes are electrically connected to the concrete structure via an electrically conductive fluid deposited on the surface of the concrete. A conductive gel or conductive liquid, such as water, may be used to create an electrically conductive pathway from the electrodes surface to the surface of the concrete allowing the measurements.

According to one embodiment, in order to ensure an optimal electrical connected to the concrete, the electrodes used in the present system comprises an interface volume, configured to be put in direct contact with the concrete surface, made of at least one material selected from the following list: natural sponges, high density sponges, water retention gels, agar-agar, high density foam and/or conductive polymer gel. The electrodes comprising materials having physical ability of retaining fluid may be immerged in a conductive fluid, such as water, before use so as to improve the electrically connection between the system and the concrete structure.

According to one embodiment, the electrodes are positioned in the predefined spatial configuration by being fixed movably or unmovably on a mechanical support. Said mechanical support may comprise a flat surface on which the electrodes are fixed.

According to one embodiment, the electrodes are disposed on a line and preferably equally spaced. This specific configuration has the advantage of allowing to obtain information concerning characteristics of the concrete structure in multiple zones located beneath said line. This information, processed by the image reconstruction module, provides an image in depth of the concrete structure as bidimensional representation of the distribution of at least one characteristic of the concrete structure.

The positioning of electrodes may be variated so as to obtain various spatial configurations wherein inter-electrode distance variates. The variation of this parameter influences the spatial resolution of the measurement.

In one example where a large number of electrodes are comprised in the system (i.e. superior to 10 electrodes), the electrodes may be disposed in a matrix comprising at least two rows of aligned electrodes. In such a spatial configuration, the inter-electrodes distance may be uniform between and along the rows or the inter-electrodes distance along the rows may be constant while the distance between the rows may variate.

According to one embodiment, each of the electrodes of the system is configurable to take the role of an emitting electrode or a receiving electrode. In one embodiment, the system comprises a switch module which is configured to automatically direct current through the emitting electrodes, under the control of the acquisition module, According to one embodiment, the configuration of the electrodes is pre-programmed and/or reprogrammable so as to take the role of injection electrode or a receiving electrode during a set of measures.

The combination of the various spatial configuration and interchangeability of electrodes role between emission and reception may be used to obtain various type of arrays such as Wenner, Wenner-Schlumberger, multiple-gradient, dipole-dipole (commonly used in geophysics). Each of these types of array is characterized by a different relation between the position of the pairs of receiving electrodes and their position with respect to the concrete structure determining the position of the effective explored zone, having its own signal to noise ratio According to one embodiment, the plurality of electrical signals is acquired from the multiple pairs of receiving electrodes sequentially or simultaneously. However, more complex electronics with a higher number of input channels is necessary for the implementation of the acquisition from multiple pairs of receiving electrodes simultaneously According to one embodiment, the injected plurality of electrical signals is configured to perform a galvanostatic pulse method or a time-domain induced polarization method. Both methods consist of injecting a direct current during a given time period and measuring the transient potential until reaching a steady state. Usually galvanostatic pulse method is used in electrochemistry, where calculations are performed during the charge and not the discharge, while the time-domain induced polarization method is more commonly used in geophysics. In one embodiment, it is not chargeability that is determined but the polarization resistance by using an electrical equivalent circuit or a curve fitting from the transient potential.

Time-domain induced polarization consists of measuring the voltage decay after the cessation of transmitted current. The area under a designated portion of the decay curve can be integrated and offered as an IP measurement of chargeability. Alternatively, IP data can be given as discrete values along the decay curve at specified times. The voltage decay is always measured for both positive and negative polarities to avoid DC offsets due to self-potential and telluric currents.

According to one embodiment, the system comprises a robotic module configured to move the system with respect to the concrete surface, especially on the concrete structure surface.

In one embodiment, the robotic module comprises gripping means configured to grip the system, still or in movement, to the concrete surface for any orientation of the concrete surface with respect to the grown. This feature allows the automatization of a series of measures for the monitoring of surfaces of a concrete structure which are not planar or not horizontal, such as walls of pillars.

According to one embodiment, the system comprising the robotic module is configured to iterate a measurement routine for monitoring a region of the concrete structure, said routine comprising:
  a displacement phase wherein the robotic module moves the system according to a predefined pitch;
  a measurement phase wherein the acquisition module acquires a plurality of electrical signals and stores the signals together with the information related to the location of the electrodes at the time of acquisition of each signal.

According to the embodiment wherein the system comprises the robotic module, the image reconstruction module is configured to generate tridimensional (3D) image of the explored zones or region of the concrete structure.

According to one embodiment, the processing module pre-process the plurality of electrical signals and process at least one output characteristic of the concrete structure associated which are used by the image reconstruction module, in combination with information of the location of the electrodes at the time of acquisition of each signal, to reconstruct a 3D image.

According to one embodiment, the system further comprises a display module configured to display the images generated by the image reconstruction module.

The present invention further relates to a method for monitoring a concrete structure comprising a reinforcement bar, said method comprising the following steps:
  receiving a plurality of electrical signals, originating from an explored zone of the concrete structure, acquired using electrochemical measurement system comprising at least six electrodes;
  receiving a model comprising a geometric disposition of the reinforcement bar in the concrete structure, initial values of resistivity and chargeability for the reinforcement bar volumes and initial values of resistivity and chargeability for the concrete volumes;
  using the model to calculate for each plurality of electrical signals at least one induced polarization potential response value and one apparent resistivity value, and from these values, process at least one output characteristic of the concrete structure associated to each explored zone from which the plurality of signals originates; wherein one output characteristic of the concrete structure is the corrosion rate of the reinforcement bar;
  generating an image of the distribution of the output characteristics of the concrete structure in the explored zones.

According to one embodiment, the method further comprises obtaining a distribution of the polarization resistance from the apparent resistivity then to obtain the corrosion rate.

As described for the system above, the six electrodes at least two emitting electrodes configured to inject a plurality of electrical signals into the concrete structure and at least four receiving electrodes configured to be combined in pairs and receive the plurality of electrical signals originating from an explored zone of the concrete structure.

The plurality of electrical signals may be obtained from one configuration and spatial disposition of the electrodes of the system or from a succession of measurement of multiple electrical signals obtained from different spatial disposition of the electrodes. For example, when the electrodes of the system are disposed inline, it is possible to acquire multiple measurements displacing the system in the direction of the line of electrodes. When this type of multiple measurements is performed the analysis of the plurality of electrical signals acquired allows to reconstruct 2D images of the explored zone.

The present invention further relates to an assembly comprising at least two systems mechanically coupled so as to form a longitudinal series of electrodes or multiple parallel lines of electrodes.

The system and assembly of the present invention may be used to monitor concrete structures such as concrete walls or pillars, concrete slabs, bunker, harbors, bridges, floors, a jetty, or a ramp, and any other building structure made of concrete.

In the present invention, the following terms have the following meanings:
- "Electrode" refers to a conductor through which electricity enters or leaves an object, substance, or region.
- "Self-potential" refers to natural potential differences resulting from electrochemical reactions in the subsurface.

BRIEF DESCRIPTION OF THE DRAWINGS

The following detailed description will be better understood when read in conjunction with the drawings. For the purpose of illustrating, the system is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Features and advantages of the invention will become apparent from the following description of embodiments of a system, this description being given merely by way of example and with reference to the appended drawings in which.

While various embodiments have been described and illustrated, the detailed description is not to be construed as being limited hereto. Various modifications can be made to the embodiments by those skilled in the art without departing from the true spirit and scope of the disclosure as defined by the claims.

DETAILED DESCRIPTION

Figure 1:
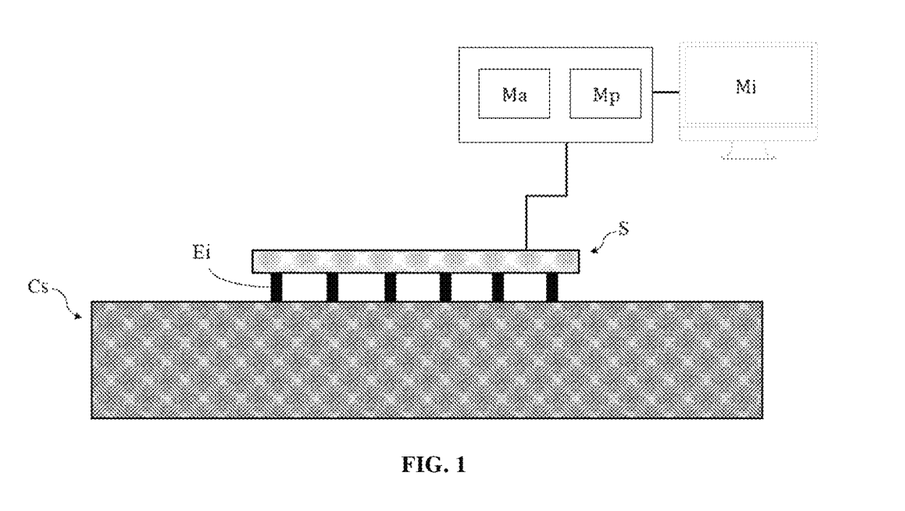
FIG. 1 is a schematic representation of a concrete structure on which is placed the system of the invention according to a first embodiment.

As shown in FIG. 1, the electrochemical measurement system S for monitoring a concrete structure Cs, according to the first embodiment, comprises six electrodes Ei configured to be placed in contact with a surface of the concrete structure which are placed on a surface of a concrete structure Cs.

In this embodiment, the system S further comprises an acquisition module Ma configured to control the electrodes Ei so as to inject a plurality of electrical signals I in the concrete structure and to acquire from it a plurality of electrical signals Si which are stored in a memory.

The system S comprises also a processing module Mp for processing the acquired signal so as to extract information on the characteristic of the concrete structure Cs and an image reconstruction module Mi for showing such information.

Figure 2:
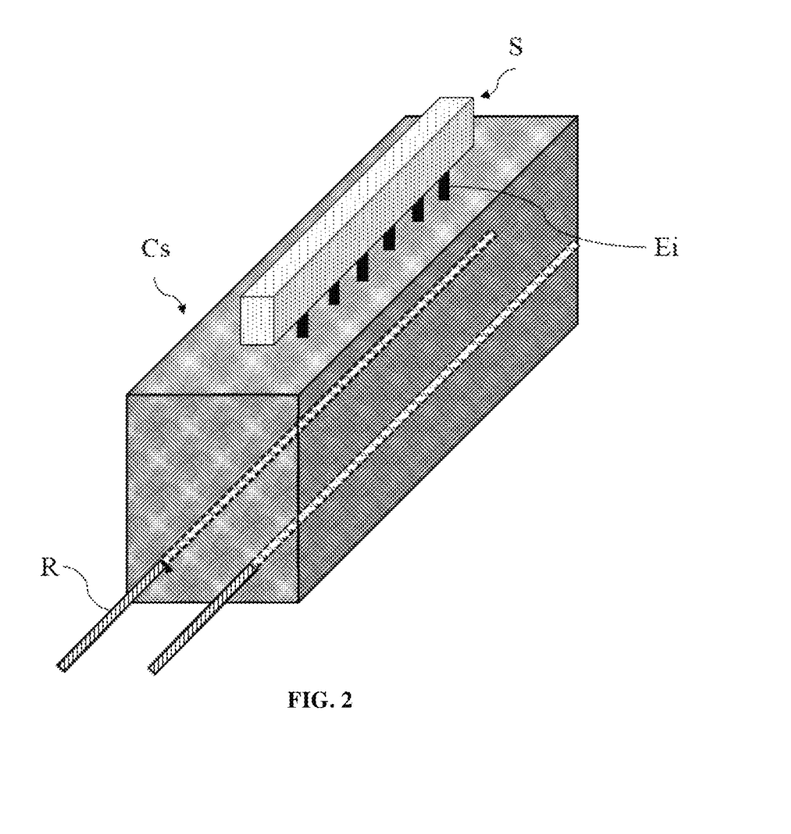
FIG. 2 is a schematic representation of a concrete structure comprising reinforcement bars on which is placed the system of the invention according to a first embodiment.

As shown in FIG. 2, the electrodes Ei are aligned, equally spaced and fixed on a mechanical structure. In order to monitor the corrosion rate of the rebars R of the concrete structure Cs, the system S is placed on the concrete structure surface in proximity of the rebars.

Figure 3:
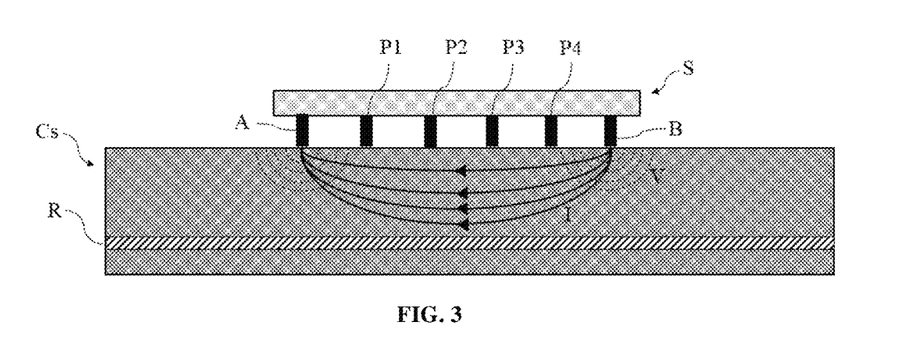
FIG. 3 is a cross section of the concrete structure and the system of FIG. 2.

FIG. 3 shows the system according to the first embodiment, comprising two emitting electrodes A and B configured to inject a plurality of electrical signals I into the concrete structure, represented by the lines of current flow. In this configuration, the emitting electrodes are disposed each on one end of the mechanical structure.

The four receiving electrodes P1, P2, P3 and P4 are fixed along the mechanical structure between the emitting electrodes A and B.

The acquisition module is configured to control the plurality of electrical signals I injected into the concrete structure using the emitting electrodes A and B. The acquisition module is configured to combine the receiving electrodes P1, P2, P3 and P4 in pairs, using all the possible combinations (i.e. P1-P2, P1-P3, P1-P4, P2-P3, P2-P4, P3-P4), so as to measure from each pair of electrodes a plurality of electrical signals (S12, S13, S14, S23, S24, S34), originating from one explored zone of the concrete structure. The explored zone is located beneath the axis connecting the electrodes in the pair at a depth depending on the distance between the two electrodes in the pair.

This embodiment is particularly advantageous as it allows to recovery information on the concrete structure beneath the system which allows the reconstruction of a bidimensional (2D) image of an in-depth section of the concrete structure.

Figure 4:
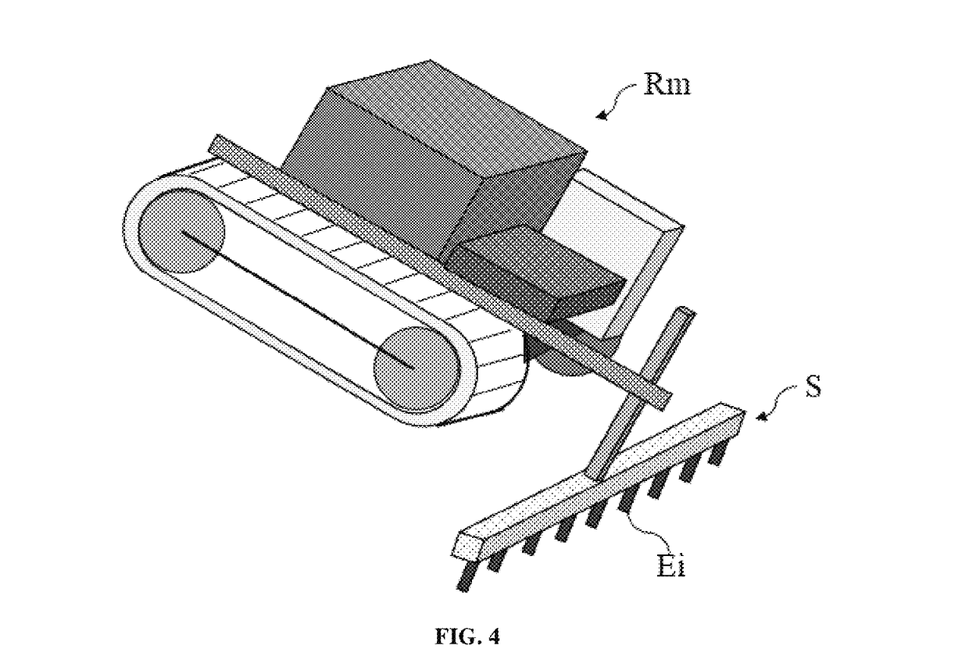
FIG. 4 is a schematic representation of a robotic module comprising a system having the electrodes disposed in a linear predefined spatial configuration.

FIG. 4 shows a second embodiment of the invention where the system S comprises a robotic module Rm.

According to this second embodiment, the system S is mechanically fixed on a track-driven robotic module Rm configured to move the system with respect to the concrete surface. The continuous track and the road wheel of the robotic module are configured to move of concrete structures having various surface geometries disposed from the horizontal to the vertical direction.

The system S in this embodiment comprises aligned electrodes Ei, equally spaced and fixed on a mechanical structure as for the embodiment shown in FIG. 2.

The system S further comprises an articulated arm on which is mechanically and removably fixed, through a holding arm, the mechanical structure on which are fixed the electrodes. The articulated arm comprises a support element, connecting the robotic module Rm to the holding arm. The holding arm is pivotally fixed to the support element so that the position of the mechanical structure on which are fixed the electrodes may be modified between a measurement position, where the electrodes must be in contact with the concrete structure to allow acquisition of electric signals from the concrete, and a movement position, where the electrodes must be raised so as to easily displace the robotic module.

EXAMPLES

The present invention is further illustrated by the following examples.

Example 1

Experiments were performed in laboratory on a CEM I mortar sample (52×34×13 cm, w/c=0.4) with one carbon steel rebar (60 cm, Φ=12 mm, cover depth=4 cm), with constant relative humidity and temperature. The carbon steel rebar was in passive conditions.

Measurements were performed in time-domain using four stainless steel electrodes in Wenner configuration; the two outer emitting electrodes (A, B) were used for the injection of a current of 100 µA and the two inner receiving electrodes (P1, P2) for measuring the potential difference. The interelectrode spacing was 15 cm (i.e. 45 cm between the two emitting electrodes) in order to ensure that the entire rebar is polarized.

The experimental protocol consists of performing ten current square wave, as follow:
  injection of 100 µA on electrode A during a time period of 30 s;
  no injection during a time period of 30 s;
  injection of −100 µA on electrode A during a time period of 30 s;
  no injection during a time period of 30 s.

Figure 5:
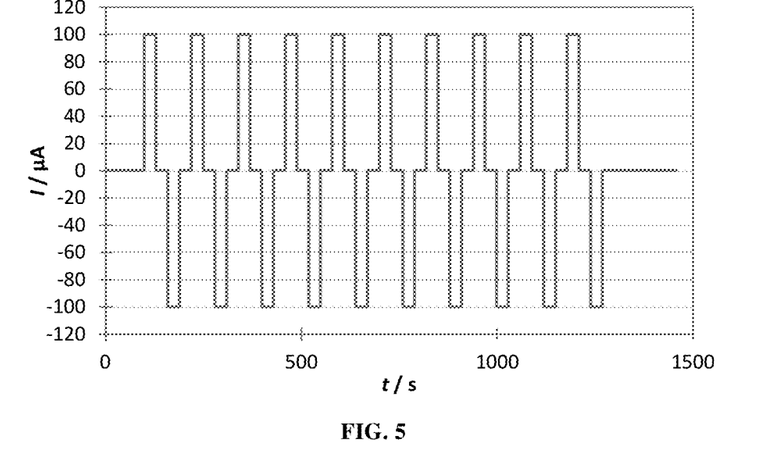
FIG. 5 is an example of a plot of the current as a function of time.
Figure 6:
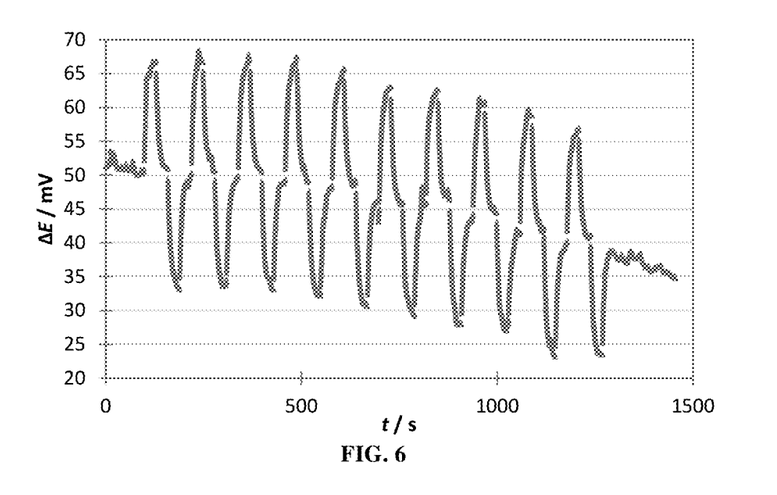
FIG. 6 is an example of a plot of the potential difference as a function of time.

FIG. 5 presents the evolution of the current with time and FIG. 6 presents the evolution of the potential difference with time when performing the measurements.

The continuous derivation of the self-potential is observed, as visible in FIG. 6 where the baseline of the potential difference constantly decreases during time.

Figure 7:
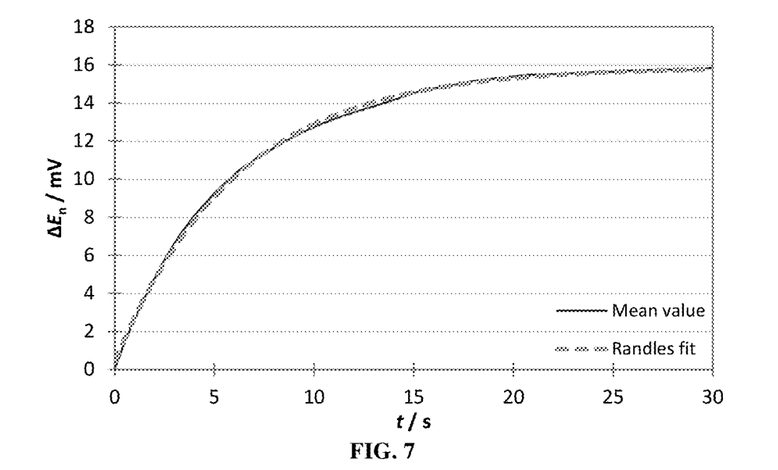
FIG. 7 is an example of a plot of the average and normalized value of the potential difference as a function of time, calculated from the ten potential difference slots shown in FIG. 6.

An average and normalized value of the potential difference obtained for the ten slots is then calculated during the charge, as shown in FIG. 7. A curve fitting based on the Randles circuit—R(CR)—is finally used to determine the concrete resistance, the polarization resistance and the double layer capacitance, using Equations. 5-8.

Considering that all the injected current polarizes the rebar, the results obtained from the fitting are:
  $R_\Omega$=13.8Ω, i.e. $\rho_\Omega$=13 Ω·m considering k=2πa;
  $C_{dl}$=0.037 F;
  $R_p$=158Ω.

To convert the polarization resistance $R_p$ in current corrosion $I_{corr}$, the Stern-Geary relation was used (see Eq. 3), with a B value of 0.052 V (passive conditions), obtaining a value of $I_{corr}$ equal to 329 µA.

The corrosion current $I_{corr}$ was then converted in corrosion rate in term of penetration rate using the following equation:

$$v_{corr} = \frac{I_{corr}M}{nA\rho F} \qquad \text{(Eq. 14)}$$

where M is the molar mass of iron (g/mol), n is the number of electrons exchanged in the reaction (n=2), A is the geometrical surface of the rebar (cm$^2$), ρ is the density of steel (g/cm$^3$) and F is the Faraday constant (96485 C/mol).

Here, considering that the entire rebar embedded in the concrete is polarized, the geometrical area is 196 cm$^2$. Hence, applying equation 14 the corrosion rate is 19.7 µm/year.

However, this result does not represent the real corrosion rate as only a part of the applied current will polarize the rebar. To determine the polarizing current, the plurality of signal must be inverted.

Example 2

Experiments were performed in laboratory on a CEM I mortar sample (52×34×13 cm, w/c=0.4) with one carbon steel rebar (60 cm, Φ=12 mm, cover depth=4 cm), with constant relative humidity and temperature. The carbon steel rebar was in passive conditions.

Measurements were performed in frequency-domain using four stainless steel electrodes in Wenner configuration; the two outer emitting electrodes were used for the injection of 100 µA RMS (alternating current) and the two inner receiving electrodes for measuring the potential difference. The interelectrode spacing was 15 cm in order to ensure that the entire rebar is polarized.

The frequencies range from 10 Hz to approximately 10$^{-3}$ Hz (3.6 mHz). Measurement at each frequency was realized three times and the mean value was reported.

Figure 8:
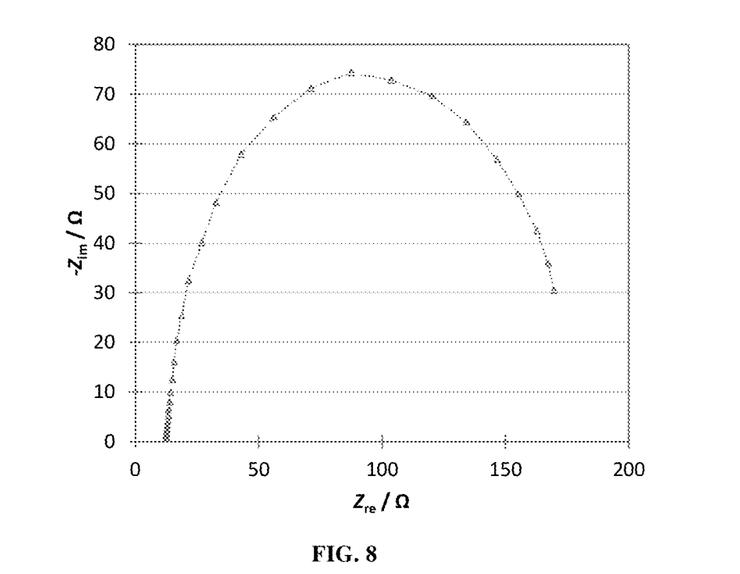
FIG. 8 is an example of a plot of the imaginary impedance as a function of the real impedance as a function of the frequency.
Figure 9:
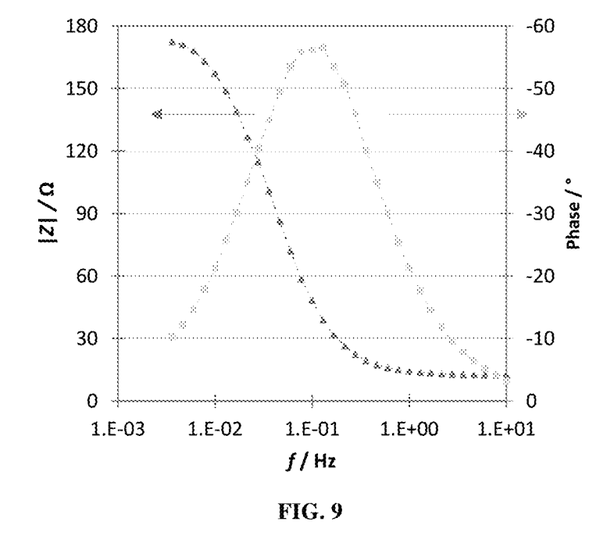
FIG. 9 is an example of a plot of the impedance modulus and the phase shift as a function of the frequency.

Results are presented as Nyquist plot (FIG. 8), showing the imaginary part of the impedance as a function of the real part of the impedance, and as Bode plot (FIG. 9) showing the modulus of the impedance and the phase shift as a function of the frequency.

An electrical equivalent circuit (EEC) was used to fit the experimental results. For this example, the selected EEC was R(QR). Considering that all the current polarizes the rebar, the results are:

$R_\Omega = 12.4 \Omega$;
$Q = 0.035$ F;
$\alpha = 0.94$;
$R_p = 166 \Omega$.

To convert the polarization resistance $R_p$ in current corrosion $I_{corr}$, the Stern-Geary relation was used (Eq. 3), with a B value of 0.052 V (passive conditions), obtaining 313 μA.

The corrosion current $I_{corr}$ was then converted in corrosion rate in term of penetration rate using the equation 14, considering that the entire rebar embedded in the concrete is polarized, the geometrical area is 196 cm² so as to obtain a corrosion rate of 18.8 μm/year.

However, this result does not represent the real corrosion rate as only a part of the applied current will polarize the rebar. To determine the polarizing current, the distribution of the current has to be modeled considering several parameters, especially the resistivity of the concrete and the cover depth.

Example 3

Acquired signals from example 2 were used to reconstruct an image of the distribution of concrete and rebar.

Figure 11:
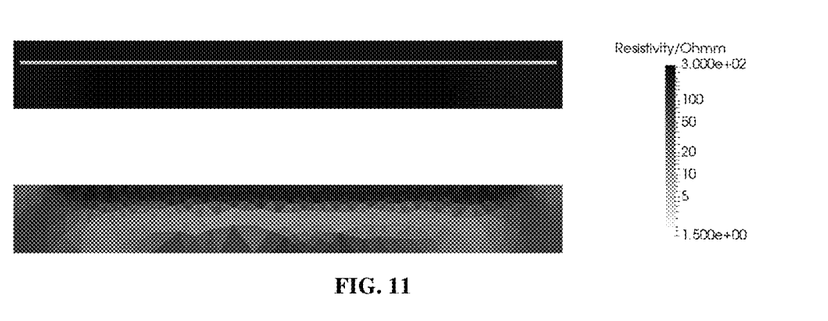
FIG. 11 is an illustration of the reconstructed image of a sample when inversion method is run with (top) or without (bottom) decoupled inversion. Resistivity in the sample is shown in a grey scale, with values ranging from 1.5 Ohm·m (light grey) to 300 Ohm·m (dark grey).

In a first reconstruction, a standard smoothness-constrained inversion is run, yielding bottom image of FIG. 11. Although a low resistivity structure is identified (in light grey), it is not accurately located.

In a second reconstruction, decoupled inversion has been used. In the starting model, concrete has a resistivity of 200 Ohm·m and rebar has a resistivity of 1.7 Ohm·m (low corrosion conditions). Image obtained is shown on top of FIG. 11. A structure of low resistivity is identified and very precisely located.

REFERENCES

A and B—emitting electrodes;
Cs—concrete structure;
Ei—electrodes;
Ma—acquisition module;
P1, P2, P3, P4—receiving electrodes;
Mi—image reconstruction module;
Mp—processing module
R—reinforcement bar;
Rm—robotic module;
S—electrochemical measurement system;

The invention claimed is:

1. An electrochemical measurement system for monitoring a concrete structure comprising a reinforcement bar, said system comprising:
at least six electrodes configured to be placed in contact with a surface of the concrete structure and arranged in a predefined spatial configuration; comprising:
at least two emitting electrodes configured to inject a plurality of electrical signals into the concrete structure;
at least four receiving electrodes configured to be combined in pairs; wherein each pair of electrodes receives a plurality of electrical signals, originating from an explored zone of the concrete structure;
an acquisition module configured (i) to control the emitting electrodes and receiving electrodes, and (ii) to acquire and store in a memory the plurality of electrical signals;
a processing module configured to:
calculate apparent resistivity values and apparent chargeability values for each plurality of electrical signals;
receive a model comprising a geometric disposition of the reinforcement bar in the concrete structure, initial values of resistivity and chargeability for the reinforcement bar volumes and initial values of resistivity and chargeability for the concrete volumes;
perform inversion using the model, the apparent resistivity values and the apparent chargeability values so as to obtain the inversed resistivity values and the inversed chargeability values, and from these values, process at least one output characteristic of the concrete structure associated to each explored zone from which the plurality of signals originates; wherein one output characteristic of the concrete structure is the corrosion rate of the reinforcement bar; and
an image reconstruction module configured to generate an image of the distribution of the output characteristics of the concrete structure in the explored zones.

2. The system according to claim 1, wherein the corrosion rate value is obtained from the induced polarization potential response value corrected by the apparent resistivity value.

3. The system according to claim 1, wherein the processing module is configured to obtain a distribution of the polarization resistance from the apparent resistivity then to obtain the corrosion rate.

4. The system according to claim 1, wherein in one predefined spatial configuration the electrodes are disposed inline.

5. The system according to claim 1, wherein the image generated represents the distribution of the at least one output characteristic of the concrete structure for an in-depth section of the concrete structure below the aligned electrodes.

6. The system according to claim 1, wherein the at least one output characteristic of the concrete structure is at least one of:
cracking, crazing, blistering, delamination, chalking,
air void,
corrosion,
water content or
a transport characteristic selected from the group comprising permeability, diffusivity or porosity.

7. The system according to claim 1, wherein the processing module is further configured to estimate a self-potential and/or electrical impedance value.

8. The system according to claim 1, wherein the plurality of electrical signals is acquired from the multiple pairs of receiving electrodes sequentially or simultaneously.

9. The system according to claim 1, wherein the injected plurality of electrical signals is configured to perform a galvanostatic pulse method or a time-domain induced polarization method.

10. The system according to claim 1, wherein the electrodes are electrically connected to the concrete structure via an electrically conductive fluid deposited on the surface of the concrete.

11. The system according to claim 1, wherein each of the electrodes of the system is configurable to take the role of an injection electrode or a receiving electrode.

12. The system according to claim 11, wherein the configuration of the electrodes is pre-programmed and/or reprogrammable.

13. The system according to claim 1, further comprising a robotic module configured to move the system with respect to the concrete surface.

14. The system according to claim 13, being configured to iterate a measurement routine for monitoring a region of the concrete structure, said routine comprising:
- a displacement phase wherein the robotic module moves the system according to a predefined pitch;
- a measurement phase wherein the acquisition module acquires a plurality of electrical signals and stores the signals together with information related to the location of the electrodes at the time of acquisition of each signal.

15. The system according to claim 14, wherein the image reconstruction module is configured to generate a tridimensional image of the explored zones or region of the concrete structure using the stored signals and the information related to the location of the electrodes at the time of acquisition of each signal.

16. An assembly comprising at least two electrochemical measurement systems for monitoring a concrete structure comprising a reinforcement bar, wherein the at least two systems are mechanically coupled so as to form a longitudinal series of electrodes or multiple parallel lines of electrodes; each system comprising:
- at least six electrodes configured to be placed in contact with a surface of the concrete structure and arranged in a predefined spatial configuration; comprising:
  - at least two emitting electrodes configured to inject a plurality of electrical signals into the concrete structure;
  - at least four receiving electrodes configured to be combined in pairs; wherein each pair of electrodes receives a plurality of electrical signals, originating from an explored zone of the concrete structure;
  - wherein the emitting electrodes and the receiving electrodes are disposed inline;
- an acquisition module configured (i) to control the emitting electrodes and receiving electrodes, and (ii) to acquire and store in a memory the plurality of electrical signals;
- a processing module configured to:
  - calculate apparent resistivity values and apparent chargeability values for each plurality of electrical signals;
  - receive a model comprising a geometric disposition of the reinforcement bar in the concrete structure, initial values of resistivity and chargeability for the reinforcement bar volumes and initial values of resistivity and chargeability for the concrete volumes;
  - perform inversion using the model, the apparent resistivity values and the apparent chargeability values so as to obtain the inversed resistivity values and the inversed chargeability values, and from these values, process at least one output characteristic of the concrete structure associated to each explored zone from which the plurality of signals originates; wherein one output characteristic of the concrete structure is the corrosion rate of the reinforcement bar; and
- an image reconstruction module configured to generate an image of the distribution of the output characteristics of the concrete structure in the explored zones, which is an in-depth section of the concrete structure below the aligned electrodes.

17. A method for monitoring a concrete structure comprising a reinforcement bar, said method comprising the following steps:
- receiving a plurality of electrical signals, originating from an explored zone of the concrete structure, acquired using electrochemical measurement system comprising at least six electrodes;
- receiving a model comprising a geometric disposition of the reinforcement bar in the concrete structure, initial values of resistivity and chargeability for the reinforcement bar volumes and initial values of resistivity and chargeability for the concrete volumes;
- using the model to calculate for each plurality of electrical signals at least one induced polarization potential response value and one apparent resistivity value, and from these values, process at least one output characteristic of the concrete structure associated to each explored zone from which the plurality of signals originates; wherein one output characteristic of the concrete structure is the corrosion rate of the reinforcement bar; and
- generating an image of the distribution of the output characteristics of the concrete structure in the explored zones.

18. The method according to claim 17, further comprising obtaining a distribution of the polarization resistance from the apparent resistivity then to obtain the corrosion rate.

* * * * *